(12) United States Patent
Eskuri

(10) Patent No.: US 8,419,658 B2
(45) Date of Patent: Apr. 16, 2013

(54) MEDICAL DEVICE INCLUDING STRUCTURE FOR CROSSING AN OCCLUSION IN A VESSEL

(75) Inventor: Alan D. Eskuri, Hanover, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1076 days.

(21) Appl. No.: 11/470,452

(22) Filed: Sep. 6, 2006

(65) Prior Publication Data
US 2008/0097247 A1 Apr. 24, 2008

(51) Int. Cl.
*A61B 5/00* (2006.01)
*A61M 25/00* (2006.01)
*A61M 25/01* (2006.01)
*A61M 25/08* (2006.01)
*A61M 25/09* (2006.01)

(52) U.S. Cl.
USPC .................. 600/585; 604/524; 606/159

(58) Field of Classification Search .............. 600/585; 604/524; 606/159
See application file for complete search history.

(56) References Cited

U.S. PATENT DOCUMENTS

| | | | |
|---|---|---|---|
| 4,030,503 A | 6/1977 | Clark, III | |
| 4,551,292 A | 11/1985 | Fletcher et al. | |
| 4,706,671 A | 11/1987 | Weinrib | |
| 4,719,924 A * | 1/1988 | Crittenden et al. | 600/585 |
| 4,762,130 A | 8/1988 | Fogarty et al. | |
| 4,817,613 A | 4/1989 | Jaraczewski et al. | |
| 4,819,634 A | 4/1989 | Shiber | |
| 4,863,442 A | 9/1989 | DeMello et al. | |
| 4,883,458 A * | 11/1989 | Shiber | 604/22 |
| 4,946,466 A | 8/1990 | Pinchuk et al. | |
| 5,059,851 A * | 10/1991 | Corl et al. | 310/334 |
| 5,095,915 A * | 3/1992 | Engelson | 600/585 |
| 5,106,455 A | 4/1992 | Jacobsen et al. | |
| 5,108,368 A * | 4/1992 | Hammerslag et al. | 604/528 |
| 5,129,910 A * | 7/1992 | Phan et al. | 606/127 |
| 5,174,295 A * | 12/1992 | Christian et al. | 600/468 |
| 5,329,923 A * | 7/1994 | Lundquist | 600/373 |
| 5,423,799 A | 6/1995 | Shiu | |
| 5,437,288 A * | 8/1995 | Schwartz et al. | 600/585 |
| 5,507,751 A * | 4/1996 | Goode et al. | 606/108 |
| 5,738,742 A | 4/1998 | Stevens | |
| 5,772,609 A | 6/1998 | Nguyen et al. | |
| 5,820,612 A | 10/1998 | Berg | |
| 5,954,651 A | 9/1999 | Berg et al. | |
| 5,972,019 A | 10/1999 | Engelson et al. | |
| 6,004,279 A * | 12/1999 | Crowley et al. | 600/585 |
| 6,139,510 A | 10/2000 | Palermo | |
| 6,235,042 B1 | 5/2001 | Katzman | |
| 6,329,069 B1 * | 12/2001 | Azizi et al. | 428/600 |
| 6,379,334 B1 * | 4/2002 | Frassica | 604/165.04 |

(Continued)

FOREIGN PATENT DOCUMENTS

| | | |
|---|---|---|
| EP | 1586274 | 10/2005 |
| JP | 7265319 | 10/1995 |
| WO | 9710022 | 3/1997 |

*Primary Examiner* — Sean Dougherty
(74) *Attorney, Agent, or Firm* — Seager, Tufte & Wickhem, LLC

(57) ABSTRACT

Medical devices comprising a tubular member are disclosed, where the tubular member can have thread members disposed on a distal portion of the tubular member. If the medical device encounters an occlusion, the medical device can be rotated, which can allow the thread members to engage and penetrate the occlusion, in some cases forming a pathway through the occlusion.

41 Claims, 11 Drawing Sheets

U.S. PATENT DOCUMENTS

| | | |
|---|---|---|
| 6,428,489 B1 * | 8/2002 | Jacobsen et al. ............. 600/585 |
| 6,579,246 B2 * | 6/2003 | Jacobsen et al. ............. 600/585 |
| 6,591,472 B1 | 7/2003 | Noone et al. |
| 6,648,874 B2 | 11/2003 | Parisi et al. |
| 6,766,720 B1 | 7/2004 | Jacobsen et al. |
| 6,875,949 B2 | 4/2005 | Hall |
| 6,918,882 B2 | 7/2005 | Skujins et al. |
| 7,494,687 B2 * | 2/2009 | Cox ............................. 427/2.24 |
| 2002/0045855 A1 | 4/2002 | Frassica |
| 2003/0023190 A1 * | 1/2003 | Cox ............................. 600/585 |
| 2003/0069522 A1 | 4/2003 | Jacobsen et al. |
| 2003/0139763 A1 | 7/2003 | Duerig et al. |
| 2004/0010194 A1 | 1/2004 | Kamiyama |
| 2004/0167441 A1 | 8/2004 | Reynolds et al. |
| 2004/0193140 A1 | 9/2004 | Griffin et al. |
| 2006/0189896 A1 | 8/2006 | Davis et al. |
| 2006/0200047 A1 * | 9/2006 | Galdonik et al. ............. 600/585 |
| 2009/0118644 A1 * | 5/2009 | Skujins et al. ................ 600/585 |

\* cited by examiner

MEDICAL DEVICE INCLUDING STRUCTURE FOR CROSSING AN OCCLUSION IN A VESSEL

FIELD OF TECHNOLOGY

The invention relates generally to medical devices. More specifically, the invention relates to intracorporal medical device, such as a guidewire, catheter, or the like, including structure for crossing an occlusion in a vessel or a patient.

BACKGROUND

The use of intravascular medical devices has become an effective method for treating many types of vascular disease. In general, one or more suitable intravascular devices are inserted into the vascular system of the patient and navigated through the vasculature to a desired target site. Using this method, virtually any target site in the patient's vascular system may be accessed, including the coronary, cerebral, and peripheral vasculature. Examples of therapeutic purposes for intravascular devices include percutaneous transluminal angioplasty (PTA) and percutaneous transluminal coronary angioplasty (PTCA).

When in use, intravascular devices, such as a guidewire, may enter the patient's vasculature at a convenient location and then can be urged to a target region in the anatomy. The path taken within the anatomy of a patient may be very tortuous, and as such, it may be desirable to combine a number of performance features in the intravascular device. For example, it is sometimes desirable that the device have a relatively high level of pushability and torqueability, particularly near its proximal end. It is also sometimes desirable that a device be relatively flexible, particularly near its distal end, for example, to aid in steering.

In addition, medical devices, such as a guidewire, catheter, or the like, will sometimes confront an occlusion, such as a lesion and/or stenosis when passing through the vasculature to a target location. In some cases, the occlusion may completely block the vessel as is the case with a chronic total occlusion. The success of the procedure often depends on the ability to insert the medical device through the occlusion.

A number of different elongated medical device structures, assemblies, and methods are known, each having certain advantages and disadvantages. However, there is an ongoing need to provide alternative elongated medical device structures, assemblies, and methods. In particular, there is an ongoing need to provide alternative medical devices including structure or assemblies configured to aid in crossing an occlusion in a vessel of a patient, and methods of making and using such structures and/or assemblies.

SUMMARY OF SOME EMBODIMENTS

The invention provides several alternative designs, materials and methods of manufacturing and using alternative elongated medical device structures and assemblies.

Some example embodiments relate to a medical device, such as a guidewire, catheter, or the like, that has an elongated tubular member with one or more thread members disposed on the outer surface of the tubular member. The one or more thread members can be useful, for example, in aiding a user of the device in crossing an occlusion in a vessel of a patient. For example, when an occlusion is engaged with the medical device, a rotational force may be applied to the medical device such that the one or more thread members may engage the occlusion and may aid in pulling and/or drawing at least a portion of the medical device through the occlusion. In some embodiments, the one or more thread members can be disposed on a distal portion of the tubular member. In some embodiments, the tubular member can include an elongated tubular member that has a plurality of slots defined in at least a distal region thereof. The plurality of slots can affect the flexibility of the tubular member.

In some embodiments, the medical device can also include a core member. In some embodiments, the tubular member can define a lumen, and at least a portion of the core member can be disposed within the lumen. The thread members of some embodiments can be disposed in a spiral manner radially about the tubular member. In some embodiments, the thread members can extend around a longitudinal axis of the tubular member; for example, the thread members can extend less than one revolution, at least one revolution, or a plurality of revolutions around the longitudinal axis of the tubular member. Additionally, in some embodiments the thread members can be attached to the surface of the tubular member and in some embodiments the thread members and the tubular member can be monolithic. A number of alternative embodiments, including alternative structures and assemblies, and methods of making and using are also disclosed.

The above summary of some embodiments is not intended to describe each disclosed embodiment or every implementation of the present invention. The Figures and Detailed Description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
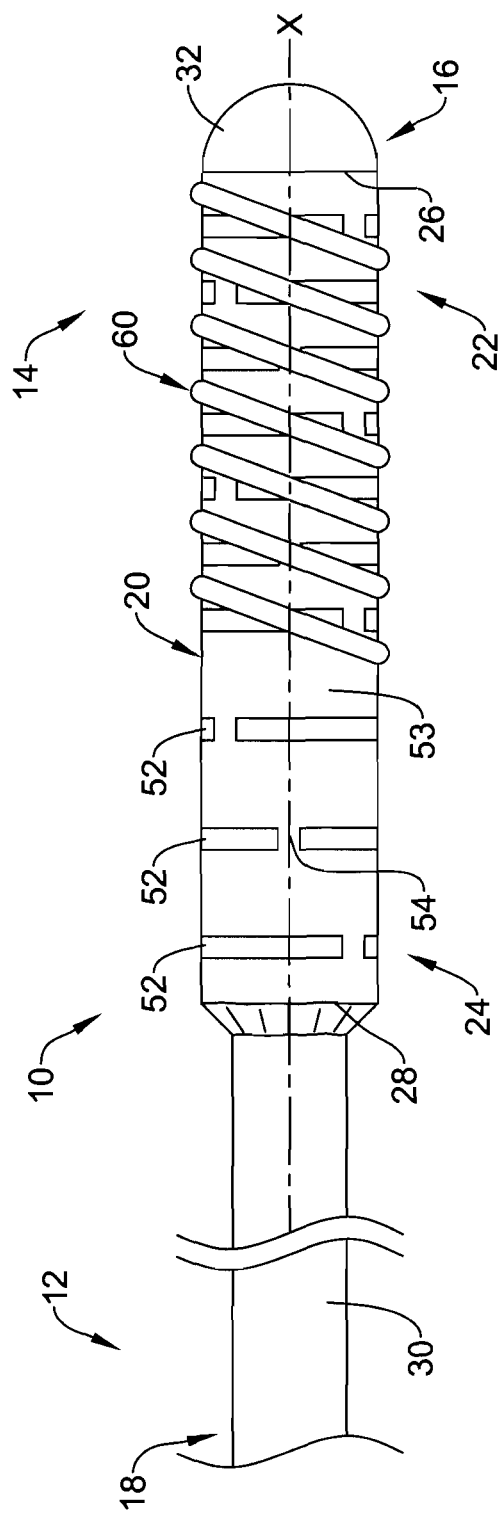
FIG. 1 is a partial perspective view of one embodiment of a guidewire.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF SOME EMBODIMENTS OF THE INVENTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

As will be appreciated, at least some embodiments relate to a medical device that includes a tubular member having one or more thread members disposed on an outside surface of the tubular member. Medical devices incorporating such a structure could be guidewires or catheters or other such medical devices. The thread members can be disposed in a generally spiral shaped pattern about a portion of the tubular member. Such a tubular member may be used, for example, in a medical device to aid in crossing an occlusion in a vessel of a patient, as will be discussed in more detail below.

Refer now to FIG. 1, which illustrates a medical device 10 in accordance with one example embodiment. In the embodiment shown, the medical device 10 is in the form of a guidewire 10. Guidewire 10 can include a proximal region 12, a distal region 14, a distal end 16, and a proximal end 18. As used herein, the proximal region 12 and the distal region 14 may generically refer to any two adjacent guidewire sections along any portion of the guidewire 10. The guidewire 10 includes a generally tubular member 20 that includes a distal section 22, a proximal section 24, a distal end 26, and a proximal end 28. The tubular member 20 may extend longitudinally along a longitudinal axis X. Some additional aspects of the tubular member 20 will be discussed in more detail below.

The guidewire 10 may also include a core member 30 that may be attached to the tubular member 20, and extend from a location within the tubular member 20 and/or from the proximal end 28 of the tubular member 20 to the proximal end 18 of the guidewire 10. However, in other embodiments, the core member 30 may be absent, and/or the tubular member 20 may extend to the proximal end 18 of the guidewire 10. For example, in some other embodiments, the tubular member 20 may extend along substantially the entire length of the guidewire 10, for example, from the proximal end 18 to the distal end 16, and the core member 30 may be present and disposed within at least a portion of the tubular member 20, or may be absent, as desired. A distal tip member 32 may be disposed at the distal end 26 of the tubular member 20 and/or the distal end 16 of the guidewire 10. The distal tip member 32 may be any of a broad variety of suitable structures, for example, a solder tip, a weld tip, a pre-made or pre-formed metallic or polymer structure, or the like, that is attached or joined to the distal end of the tubular member 20 using a suitable attachment technique.

Figure 2:
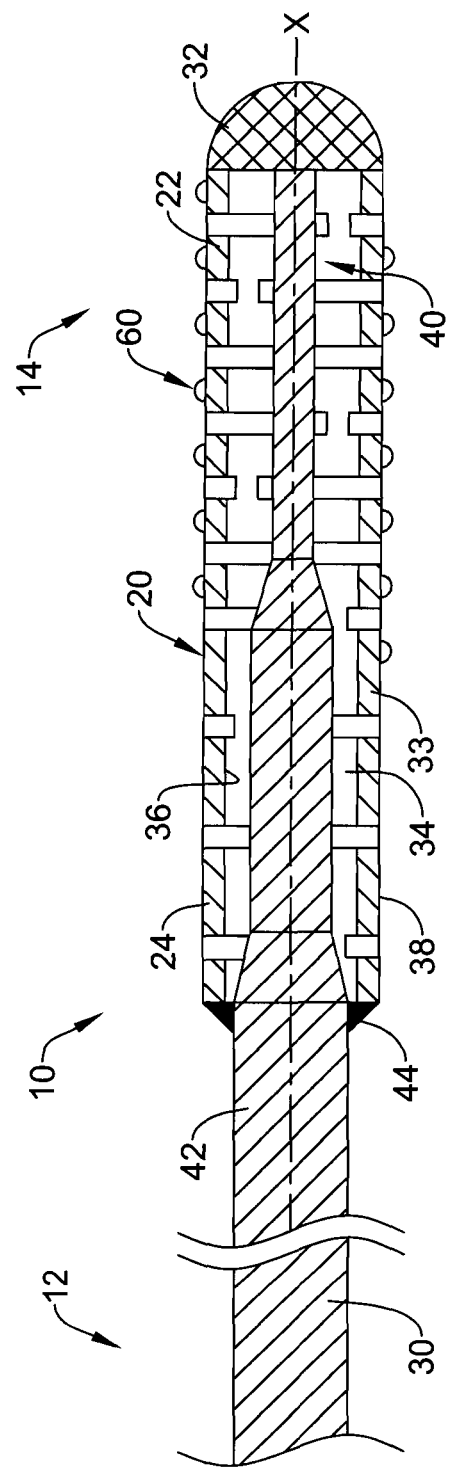
FIG. 2 is a partial cross-sectional view of the embodiment shown in FIG. 1.

Referring now to FIG. 2, the tubular member 20 includes a tubular wall 33 including an outer surface 38 and an inner surface 36 defining an inner lumen 34. As can be appreciated, a portion of the core member 30 may extend into at least a portion of the lumen 34. In the embodiment shown, the core member 30 includes a distal portion 40 that extends within the lumen 34, and a proximal portion 42 that extends proximally from the tubular member 20. The core member 30 can be attached to the tubular member 20 in any suitable manner and at any suitable location. For example, the core member 30 may be attached to the tubular member 20 through one or more attachment areas 44, which in this embodiment are disposed adjacent the proximal end 28 of the tubular member 20. It should be understood that additional attachment areas, and/or alternative positioning of attachment areas may be used in other embodiments. As shown in FIG. 2, the core member 30 may also extend to, and be attached to the distal tip member 32. In other embodiments, however, the core member 30 may end proximally from the distal tip member and/or proximally of the distal end 26 of the tubular member 20. In addition, it should be understood that other structure or components, may be used in the guidewire construction, such as a shaping wire or ribbon, one or more coils, marker members, or the like, or others, some of which are discussed below.

As indicated above, the tubular member 20 includes both a distal section 22 and a proximal section 24. In some embodiments, as shown in FIGS. 1 and 2, the tubular member 20 can be a monolithic, single and/or a one-piece structure that defines both the proximal and distal ends 22/24. The tubular structure can also be a continuous and/or uninterrupted tubular member that defines both the proximal and distal sections 22/24. In other embodiments, the tubular member 20 may include a plurality of discrete tubular components or sections that are attached to one another to form the tubular member 20, or portions thereof. For example, the distal section 22 and proximal section 24 may each be a discrete tubular component that are attached and/or secured together to create the tubular member 20. In such a case, the components may be attached using any suitable joining or bonding technique and/or structure. For example, the distal and proximal sections 22/24 may be joined using adhesive bonding, welding, soldering, brazing, mechanical bonding and/or fitting, or the like, or any other suitable technique.

In some embodiments, as shown in FIGS. 1 and 2, the outer diameter of the tubular member 20 can be the same or substantially the same along the entire length of the tubular member 20. In other embodiments, the outer diameter of the tubular member proximal section 24 and the outer diameter of the tubular member distal portion 22 can be different. For example, the outer diameter of the tubular member proximal section 24 could be smaller than the outer diameter of the tubular member distal section 22. The change in diameter can be a sharp change in the diameter, it could be step-wise, or it could be a gradual change over a length of the tubular member 20. For example, the diameter of the tubular member 20 can gradually taper along some or all of the length of the tubular member 20, or along some or all of a proximal portion of the tubular member 20.

Figure 8:
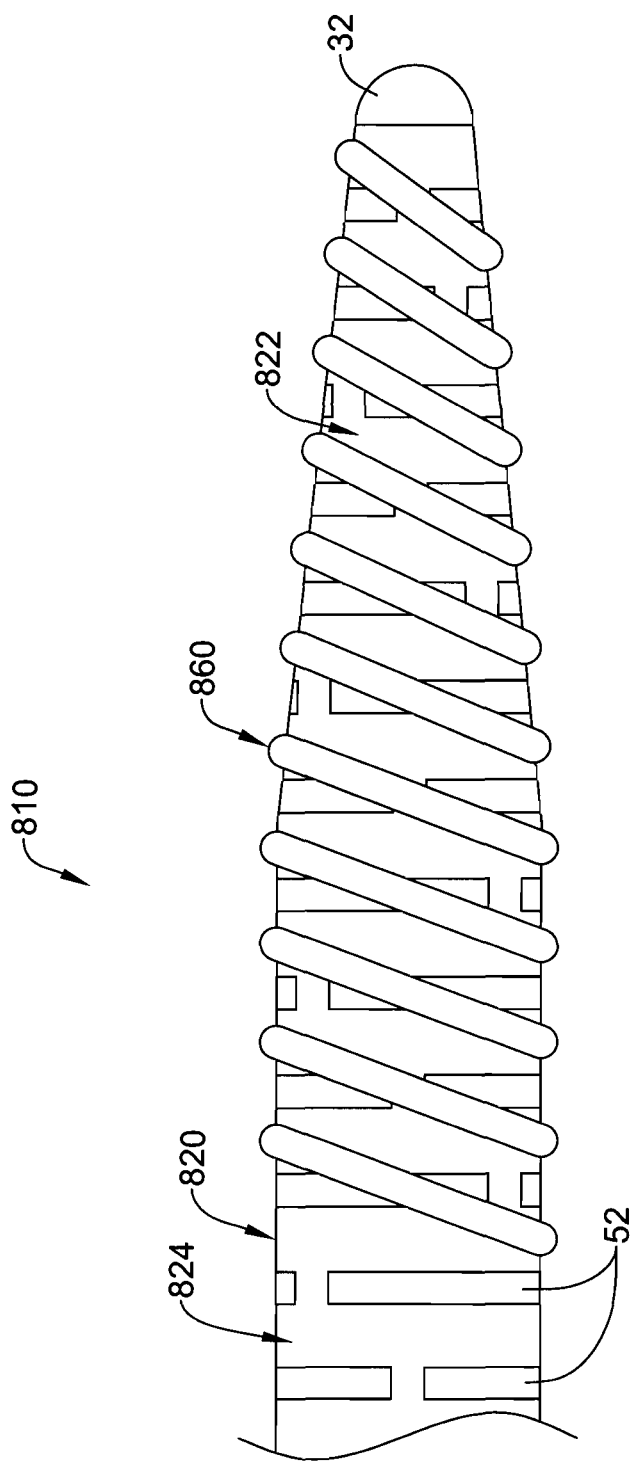
FIG. 8 is a partial cross-sectional view of another embodiment of a guidewire.

In some embodiments, a smaller diameter proximal portion of the tubular member 20 can provide for certain benefits. For example, the distal section 22, due to its greater diameter, may be better adapted to engage an occlusion in a vessel of a patient. Additionally, the proximal section 24, due to its reduced diameter relative to the distal section 22, may extend through a pathway in an occlusion created by the larger distal section 22 with a reduced amount of drag and/or engagement with the occlusion and/or other parts of the vessel. Additionally, the proximal section, due to its reduced diameter, may also be provided with greater flexibility relative to the distal section 22. These are but of few examples of some benefits that may be realized due to the distal section 22 including a greater outer diameter than the proximal section 24 of the tubular member 22. In other embodiments, however, the outer diameter of the distal section 22, or portions thereof, may be the same or smaller than the outer diameter of the proximal section, or portions thereof. For example, as shown in FIG. 8 (which is described in more detail below), the distal section can have a tapered or smaller diameter portion. In some embodiments, this distal reduction in diameter can be in addition to a separate proximal reduction in diameter of the tubular member.

In embodiments where the distal and proximal sections 22/24 are two discrete and/or separate components that are attached, the variances in the outer diameters can be provided by the use of different discrete tubular components having different outer diameters. In embodiments where the tubular member 20 is a one-piece or monolithic member, the variances in the outer diameters can be provided by grinding or otherwise working the tubular member 20 to provide the desired diameters.

The tubular member 20 can optionally include a plurality of cuts, apertures, and/or slots 52 defined in the wall 33. In some embodiments, at least some, if not all of the slots 52 are disposed at the same or a similar angle with respect to the longitudinal axis of the tubular member 20. As shown, the slots 52 can be disposed at an angle that is perpendicular, or substantially perpendicular, to the tubular member longitudinal axis X. However, in other embodiments, a group of one or more slots 52 may be disposed at different angles relative to another group of one or more slots 52.

The slots 52 may be provided to enhance the flexibility of the tubular member 20 while still allowing for suitable torque transmission characteristics. The slots or apertures 52 may be formed such that one or more rings and/or turns 53 interconnected by one or more beams 54 are formed in the tubular member 20, and such rings 53 and beams 54 may include portions of the tubular member 20 that remain after the slots 52 are formed in the body of the tubular member 20. Such an interconnected ring structure may act to maintain a relatively high degree of tortional stiffness, while maintaining a desired level of lateral flexibility. In some embodiments, some adjacent slots 52 can be formed such that they include portions that overlap with each other about the circumference of the tube 20. In other embodiments, some adjacent slots 52 can be disposed such that they do not necessarily overlap with each other, but are disposed in a pattern that provides the desired degree of lateral flexibility.

Additionally, the slots 52 can be arranged along the length of, or about the circumference of, the tubular member 20 to achieve desired properties. For example, the slots 52 can be arranged in a symmetrical pattern, such as being disposed essentially equally on opposite sides about the circumference of the tubular member 20, or equally spaced along the length of the proximal section 24 of the tubular member 20, or can be arranged in an increasing or decreasing density pattern, or can be arranged in a non-symmetric or irregular pattern. Other characteristics, such as slot size, slot shape and/or slot angle with respect to the longitudinal axis X of the tubular member, can also be varied along the length of the tubular member 20 in order to vary the flexibility or other properties. In other embodiments, moreover, it is contemplated that the tubular member proximal section 24, or the entire tubular member 20, may not include any such slots 52.

Any of the above mentioned slots can be formed in essentially any known way. For example, slots 52 can be formed by methods such as micro-machining, saw-cutting, laser cutting, grinding, milling, casting, molding, chemically etching or treating, or other known methods, and the like. In some such embodiments, the structure of the tubular member 20 is formed by cutting and/or removing portions of the tube to form slots 52. Some example embodiments of appropriate micromachining methods and other cutting methods, and structures for tubular members and medical devices including tubular members are disclosed in U.S. Pat. Publication No. US 2003/0069522, and/or U.S. Pat. No. 6,766,720, the entire disclosures of which are herein incorporated by reference. Some example embodiments of etching processes are described in U.S. Pat. No. 5,106,455, the entire disclosure of which is herein incorporated by reference.

Referring again to FIGS. 1 and 2, some embodiments of the current invention can include a tubular member 20 with a thread member 60 disposed on the tubular member 20. The thread member 60 can be disposed on the tubular member 20 by being attached to a surface of the tubular member 20 or, in the alternative, the thread member 60 and the tubular member 20 can together be a monolithic, one-piece, single and/or continuous and/or uninterrupted structure. As shown in FIG. 1, the thread member 60 can at least partially occlude or block any slots 52 that have been formed in the tubular member 20. In addition, FIG. 1 shows the thread member 60 being formed at a constant pitch. However, the pitch of the thread member 60 can also be varied with along the length of the thread member 60. For example, the pitch of the thread member 60 could increase in the distal direction, increase in the proximal direction, or the pitch could be increased along one or more intermediate portions of the thread member 60. Also, the tubular member 20 could have more than one thread member 60 disposed on it; for example, multiple thread members 60 (e.g., 2, 3, 4, 5 or 6 thread members) could be disposed on the tubular member 20, in some cases forming a screw-like pattern with multiple threads.

In the example embodiment of FIG. 1, a thread member 60 is disposed on the tubular member 20. In this example, the thread member 60 extends around the tubular member longitudinal axis X a plurality of times. Thread member 60 could also extend around the longitudinal axis X less than one revolution, one revolution, or at least one revolution. Examples of additional different thread member configurations will be discussed below. As mentioned above, and as shown in FIG. 2, the thread member 60 can be a separate structure that has been extended around and attached to the outer surface 38 of the tube wall 33. Some examples of structures that could be disposed on the outer surface 38 in such a manner are a wire, a strip of solder, or a spring or coil that can be fit over the tubular member 20. As shown in FIG. 2, the thread member 60 can extend around the outer surface 38 of the tube wall 33. In embodiments where one or more separate structures are added to the tubular member 20 to form the thread member 60, the thread member 20 can be attached using any acceptable methods; for example, the thread member structure could be attached to the tubular member by welding (including laser welding), soldering, brazing, adhesive, mechanical bonding, or the like, or combinations thereof. Also, the structures that make up the thread member 60 can be attached to he tubular member 20 along substantially the entire length of the thread member 60 or attached at a plurality of discrete locations.

Figure 3:
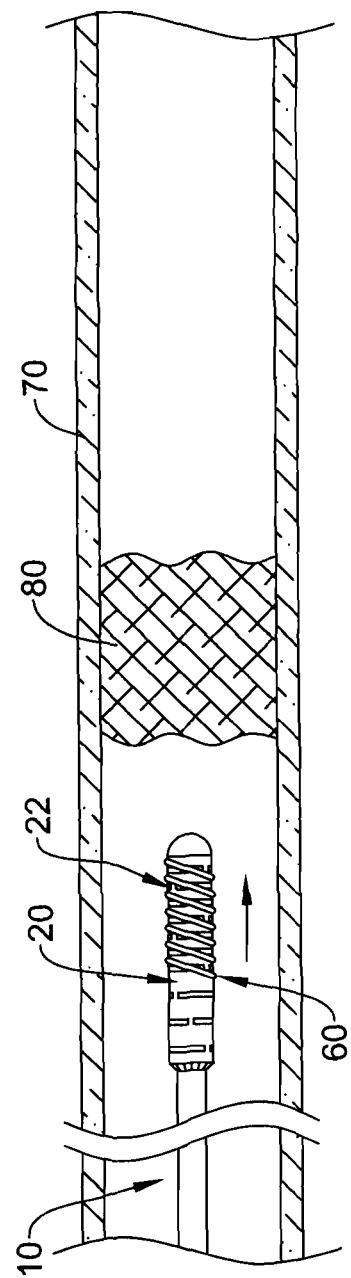
FIGS. 3-5 are diagrams showing an embodiment of a guidewire similar to the one shown in FIGS. 1 and 2 in use.
Figure 4:
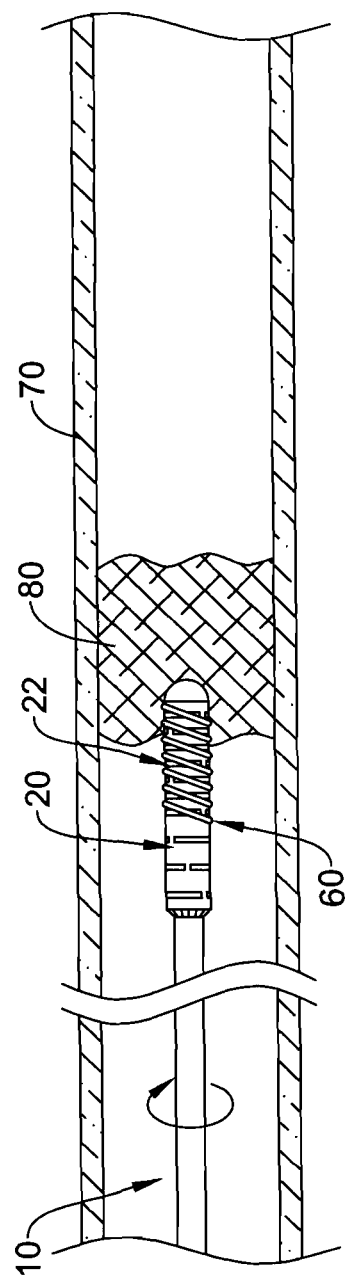
Figure 5:
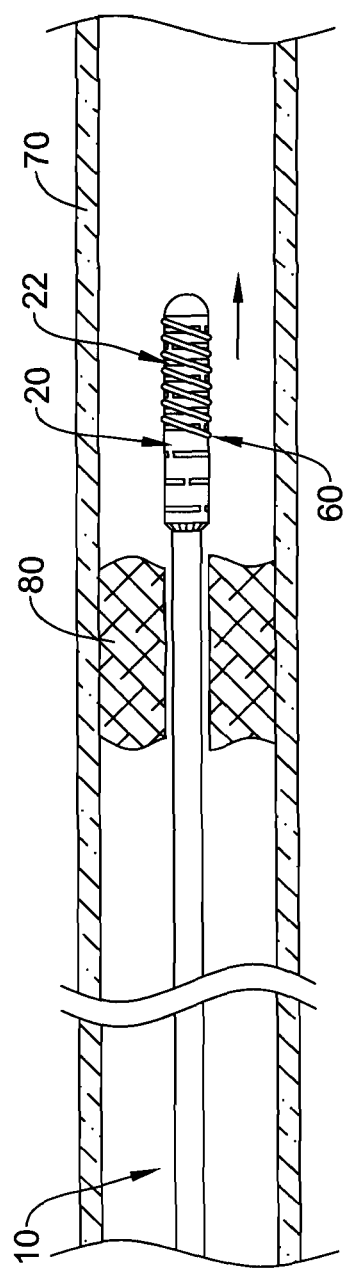
Figure 6:
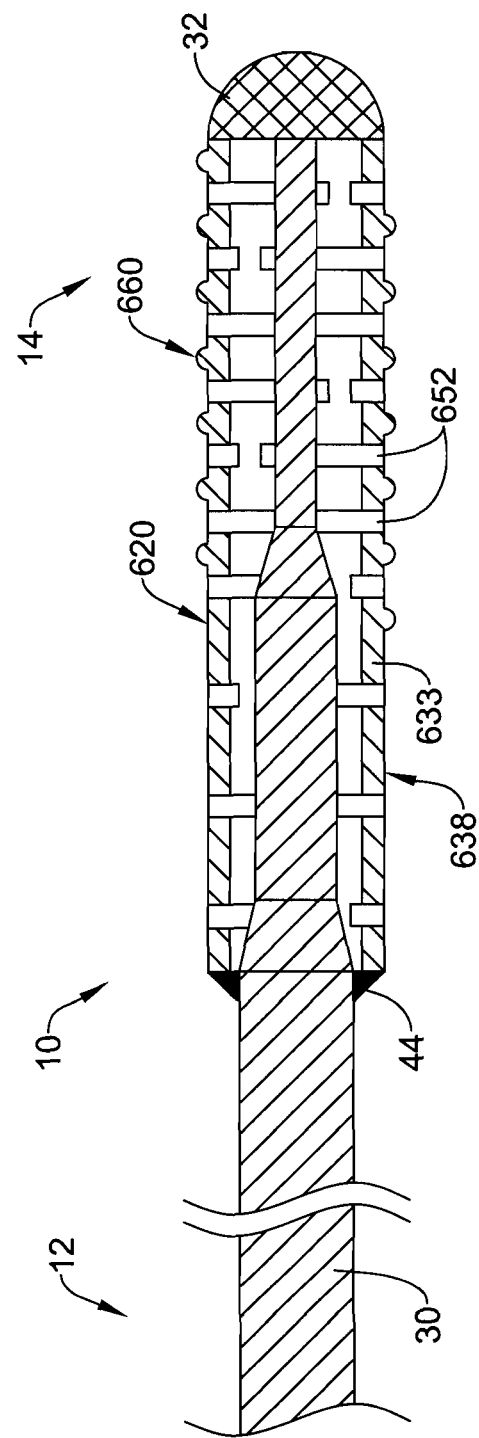
FIG. 6 is a partial cross-sectional view of another embodiment of a guidewire.

Refer now to FIGS. 3-5, which may be used in providing a discussion of one example of use of the guidewire 10. As mentioned above, the guidewire 10 may be configured to aid a user to cross an occlusion 80 in a vessel 70 of a patient. In particular, the thread member 60 disposed on the tubular member 20 of the guidewire 10 may be configured to aid in drawing and/or pulling the guidewire 10 into and/or through an occlusion. As shown in FIG. 3, the guidewire 10 may be advanced through the patient's vasculature, for example in a vessel 70, until it reaches an occlusion 80 within the vessel 70. As shown in FIG. 4, the distal section 22 of the guidewire 10 may be forced into contact with the occlusion 80. For example, the distal section 22 may be pushed slightly into the occlusion 80. As indicated by the circular arrow in FIG. 4, the guidewire 10 may be rotated such that at least part of the spiral-shaped pattern of thread member 60 engages a portion of the occlusion 80. As the guidewire 10 is rotated in a predetermined direction, the thread member 60 can engage the occlusion in a screw-like, auger-like, and/or threaded-like manner and draw and/or pull the guidewire 10 into the occlusion 80. Continued application of rotational force, in some cases in combination with lateral force, may allow the distal section to continue to screw and/or auger into the occlusion, and ultimately pass through the occlusion, as shown in FIG. 6. Once the guidewire 10 is passed through the occlusion, another device, such as a catheter, atherectomy device, distal portiction device, or the like may be threaded onto the guidewire and urged distally and passed through the occlusion 80 and/or may be used to treat the occlusion 80.

Forming the tubular member 20, or sections thereof, may include any one of a number of different techniques. For example, the tubular member 20, including the distal and proximal sections 22/24 and/or components, may be created by casting or forming methods, stamping methods, or the like, and may be shaped or otherwise worked, for example, by centerless grinding methods, into the desired shape and/or form. A centerless grinding technique may utilize an indexing system employing sensors (e.g., optical/reflective, magnetic) to avoid excessive grinding of the connection. In addition, the centerless grinding technique may utilize a CBN or diamond abrasive grinding wheel that is well shaped and dressed to avoid grabbing tubular member 20 during the grinding process. In some embodiments, tubular member 20 is centerless ground using a Royal Master HI-AC centerless grinder. In some embodiments, slots can be formed in the tubular member and thread member(s) can then be disposed on the outer surface 38 of the tubular member 20. In such a case, the thread member(s) can be formed over some of the slots, essentially covering some or all of the open areas of some of the slots. Alternatively, thread member(s) can be formed around the slots, keeping the slots open. Thread member(s) can also be disposed on the tubular member, and then slots can be formed in the tubular member. In such a case, the slots can be formed around the thread member(s), or the slots could be formed through a side wall of the tubular member and through any thread member(s), creating gaps in the thread member(s).

Another embodiment is shown in FIG. 6, wherein common reference numerals can refer to similar structure to the embodiments discussed above. In this embodiment, the tubular member 620 can have a thread member 660 that is disposed on the tubular member 620, where the thread member 660 and the tubular member 620 are together a monolithic or one-piece structure. The thread member 660 can be disposed on an outer surface 638 of the tube wall 633 that makes up the tubular member 620. In such a case, the tubular member 620 can originally be a larger diameter tubular member, and the larger diameter tubular member can be cut away, for example using any of the above-mentioned techniques, leaving the thread member 660 disposed on the surface of the tubular member 620. Slots 652 can also be formed in the tubular member 620. The slots 652 can be formed around the thread member(s), or the slots 652 can be formed through the thread member(s) and the wall of the tubular member 620, forming gaps in the thread member(s). In most other respects, the tubular member 620 can be similar to tubular member 20 in FIGS. 1 and 2. As one example, tubular member 620 can have a plurality of thread members disposed on it; for example, tubular member 620 can have 1, 2, 3, 4, 5 or 6 thread members disposed on it.

Figure 7:
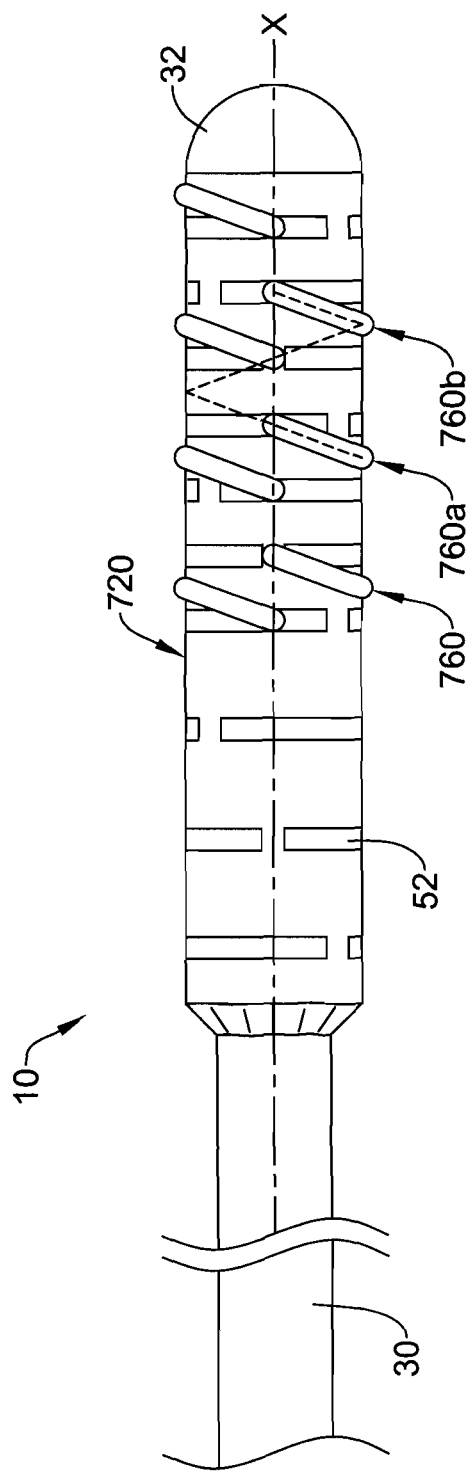
FIG. 7 is a partial perspective view of another embodiment of a guidewire.

Other configurations for the thread member(s) are also contemplated. For example, FIG. 7, shows another alternate embodiment of a guidewire, wherein common reference numbers indicate similar structure. In this example, a plurality of thread sections 760 can be disposed on the tubular member 720. The thread sections 760 can each form a thread member, or one or more of the thread sections 760 can be spirally aligned, together forming a thread member. For example, the dotted line in FIG. 7 shows how thread sections 760a and 760b can be spirally aligned, forming a discontinuous thread member. The thread sections 760 can extend around the tubular member longitudinal axis X less than one revolution, one revolution, more than one revolution, or a plurality of revolutions. The tubular member 720 can also have a plurality of thread members disposed on it; for example, tubular member 720 can have 1, 2, 3, 4, 5 or 6 thread member disposed on it. The thread configurations described with respect to FIG. 7 can be used in conjunction with any of the embodiments described herein.

FIG. 8 shows another example embodiment wherein common reference numbers indicate similar structure. The tubular member 820 can have a portion of the tubular member (for example, a portion of the tubular member proximal section 824) that has a relatively large outer diameter, and the tubular member distal section 822 that can have a reduced diameter. For example, shown in FIG. 8 is a tapered part in the distal section 822 that tapers distally to the distal end of the tubular member. It is also contemplated that the taper can end proximal of the distal end of the tubular member. In such a case, the tubular member distal section 822 can have one or more additional tapers distal of the first taper, and/or one or more constant diameter portions distal of the first taper.

Also, as mentioned above with respect to other embodiments, the tubular member proximal section 824 (only part of which is shown in FIG. 8) can have a reduced diameter portion. Such a proximal reduction in diameter can, as mentioned above, help with crossing an occlusion. In embodiments where the distal section 822 and/or proximal sections 824 and/or a distal tapered portion are discrete and/or separate components that are attached, the variances in the outer diameters can be provided by the use of different discrete tubular components having different outer diameters or shapes. In embodiments where the tubular member 820 is a one-piece and/or monolithic member, the variances in the outer diameters can be provided by grinding or otherwise working the tubular member 820 to provide the desired diameters.

The thread member 860 can be disposed on the outer surface of the tubular member 820, for example on the tapered portion of the tubular member 820. The thread member 860 can be disposed on the outer surface of the tubular member 820 from proximal of the tapered portion and along all, or just a portion of, the tapered portion. The tubular member 820 can have a single or a plurality of thread members; for example, 1, 2, 3, 4, 5 or 6 thread members 860 can be disposed on the tubular member 820. The thread member 860 disposed at least partially on a tapered portion can be useful, for example, in aiding a user in crossing an occlusion in a vessel of a patient. When the end of the medical device first comes into contact with the occlusion, the reduced diameter or tapered portion of the tubular member distal section 822 can aid in getting the tip of the medical device to initially penetrate the occlusion of the medical device, allowing the thread member 860 to engage the occlusion.

Figure 9:
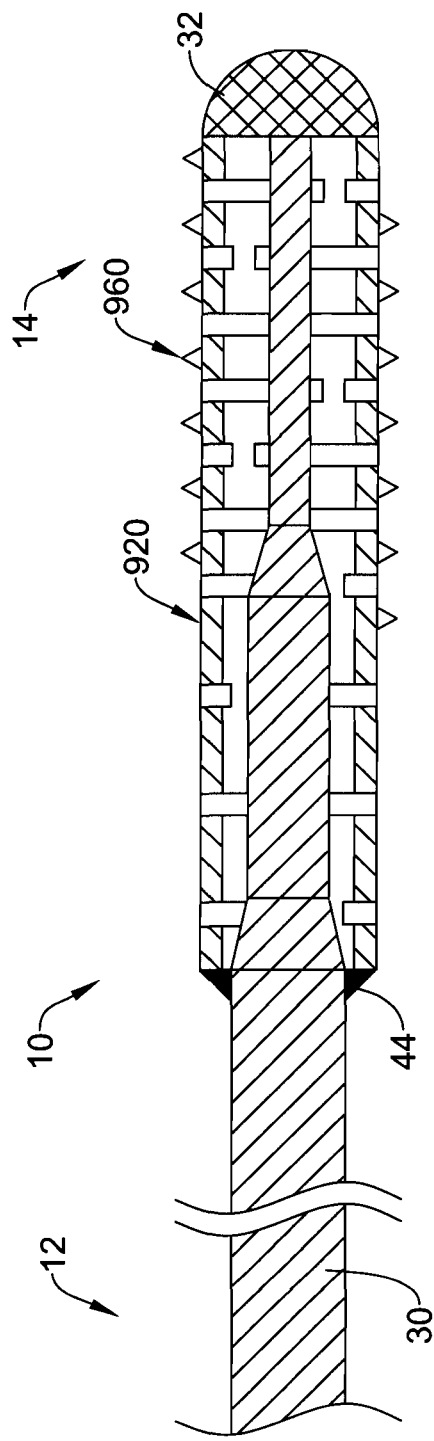
FIG. 9 is a partial cross-sectional view of another embodiment of a guidewire having an alternate cross-sectional shape of the threads.
Figure 10:
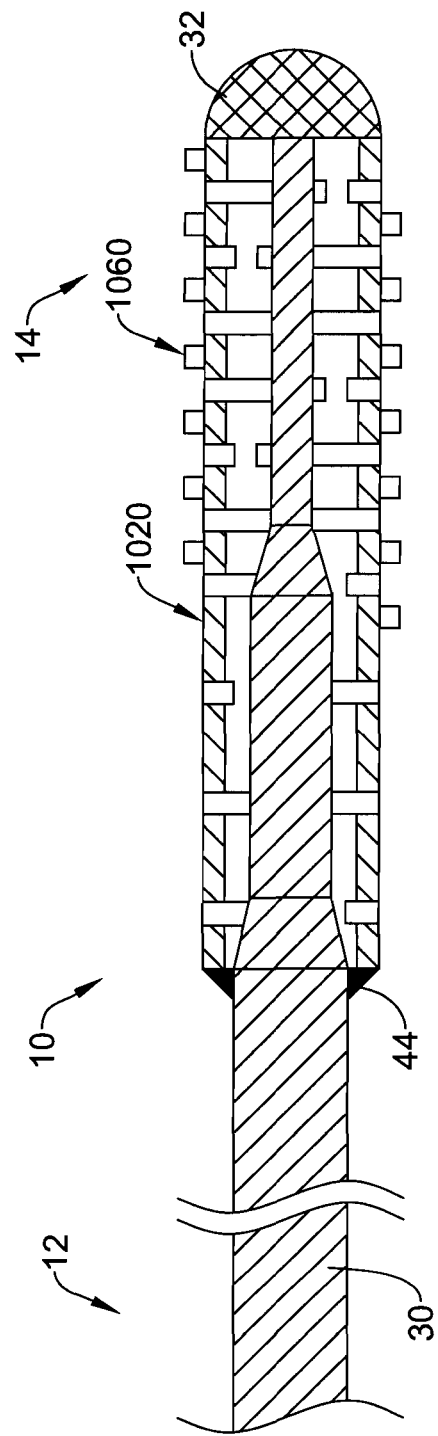
FIG. 10 is a partial cross-sectional view of another embodiment of a guidewire having another alternate cross-sectional shape of the threads.

Turning now to FIGS. 9 and 10, some alternative embodiments are shown wherein common reference numbers indicate similar structure. It should be noted that any of the variations of thread design mentioned with respect to FIGS. 9 and 10 can be used in conjunction with any of the designs described herein. One alternative design shown in these figures is the cross-sectional shape of the thread member (960, 1060) that is disposed on the tubular member (920, 1020). Thread member 960 in FIG. 9 is shown to have a triangular cross-section, as opposed to generally rounded, semi-circular cross-section shown in FIGS. 2 and 6. In addition, thread member 1060 of FIG. 10 has a square or rectangular in cross-section. The cross-sectional shapes of the thread members can have substantially any shape depending on the application or can change shape, size, height or width along the length of the one or more thread member. In embodiments with a plurality of thread members, each of the thread members can have a different cross-sectional shape, size, height or width, and/or each of the thread members can vary along their lengths, either varying in the same manner or varying differently.

Figure 11:
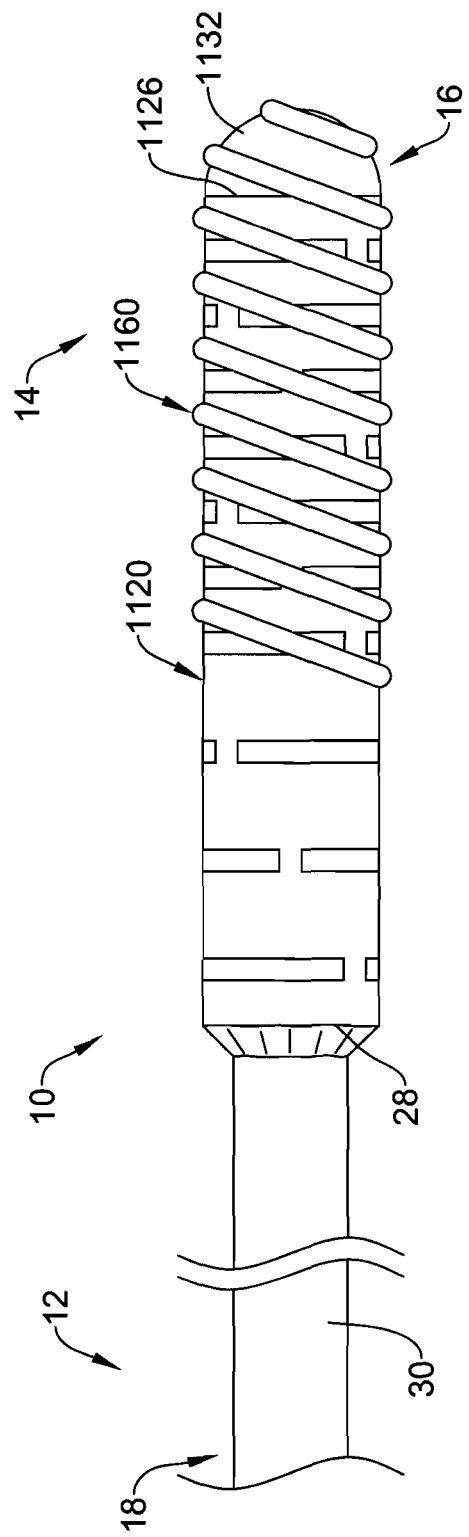
FIG. 11 is a partial perspective view of another embodiment of a guidewire.

FIG. 11 shows another example embodiment wherein common reference numbers indicate similar structure. A thread member 1160 is disposed on the tubular member 1120 from proximal of the tubular member distal end 1126 and extends onto the distal tip 1132 of the medical device. Such a design for the one or more thread member can be incorporated into any of the designs discussed in this application as desired, and, in some cases, can aid in engaging an occlusion more quickly and effectively.

A wide variety of materials and alternative features can also be used with any of the embodiments described herein. A description of some of these materials and alternative features with respect to FIGS. 1 and 2 is given below. However, it should also be understood that any of these materials and/or alternative features can also be incorporated into any of the other embodiments described herein. The materials that can be used for the various components of guidewire 10 may include those commonly associated with medical devices. For example, core member 30 and/or tubular member 20 may be made from a metal, metal alloy, a metal-polymer composite, and the like, or any other suitable material. Some examples of suitable metals and metal alloys include stainless steel, such as 304V, 304L, and 316LV stainless steel; mild steel; nickel-titanium alloy such as linear-elastic or super-elastic nitinol, nickel—chromium alloy, nickel—chromium—iron alloy, cobalt alloy, tungsten or tungsten alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), hastelloy, monel 400, inconel 625, or the like; other Co—Cr alloys; platinum enriched stainless steel; or other suitable material.

Within the family of commercially available nickel-titanium or nitinol alloys, is a category designated "linear elastic" which, although it may be similar in chemistry to conventional shape memory and superelastic varieties, exhibits distinct and useful mechanical properties. By the applications of cold work, directional stress, and heat treatment, the material is fabricated in such a way that it does not display a substantial "superelastic plateau" or "flag region" in its stress/strain curve. Instead, as recoverable strain increases, the stress continues to increase in a generally linear relationship (as compared to that of super-elastic material, which has a super-elastic plateau) until plastic deformation begins. In some embodiments, the linear elastic nickel-titanium alloy is an alloy that does not show any substantial martensite/austenite phase changes that are detectable by DSC and DMTA analysis over a large temperature range.

For example, in some embodiments, there are no substantial martensite/austenite phase changes detectable by DSC and DMTA analysis in the range of about −60° C. to about 120° C. The mechanical bending properties of such material are therefore generally inert to the effect of temperature over this very broad range of temperature. In some particular embodiments, the mechanical properties of the alloy at ambient or room temperature are substantially the same as the mechanical properties at body temperature. In some embodiments, the use of the linear elastic nickel-titanium alloy allows the guidewire to exhibit superior "pushability" around tortuous anatomy. Accordingly, components of guidewire 10 such as core member 30 and/or tubular member 20 may include linear elastic nickel-titanium alloy.

In some embodiments, the linear elastic nickel-titanium alloy is in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. In some other embodiments, a superelastic alloy, for example superelastic Nitinol can be used to achieve desired properties. In one example, the core member 30 comprises stainless steel and the tubular member 20 comprises linear elastic Nitinol. In another embodiment, the core member 30 comprises stainless steel and the tubular member 20 comprises superelastic Nitinol. In yet another embodiment, the core member can have a proximal section comprising stainless steel and a distal section comprising either linear elastic and/or superelastic Nitinol, and the tubular member 20 can comprise either linear elastic and/or super-elastic Nitinol.

In at least some embodiments, portions or all of core member 30 and/or tubular member 20, or other components that are part of or used in the device, may be doped with, made of, or otherwise include a radiopaque material. Radiopaque materials are understood to be materials capable of producing a relatively bright image on a fluoroscopy screen or another imaging technique during a medical procedure. This relatively bright image aids the user of device 10 in determining its location. Some examples of radiopaque materials can include, but are not limited to, gold, platinum, palladium, tantalum, tungsten alloy, polymer material loaded with a radiopaque filler, and the like. Additionally, radiopaque marker bands and/or coils may be incorporated into the design of guidewire 10 to achieve the same result.

In some embodiments, a degree of MRI compatibility is imparted into device 10. For example, to enhance compatibility with Magnetic Resonance Imaging (MRI) machines, it may be desirable to make core member 30 and/or tubular member 20, or other portions of the medical device 10, in a manner that would impart a degree of MRI compatibility. For example, core member 30 and/or tubular member 20, or portions thereof, may be made of a material that does not substantially distort the image and create substantial artifacts (artifacts are gaps in the image). Certain ferromagnetic materials, for example, may not be suitable because they may create artifacts in an MRI image. Core member 30 and/or tubular member 20, or portions thereof, may also be made from a material that the MRI machine can image. Some materials that exhibit these characteristics include, for example, tungsten, Elgiloy, MP35N, nitinol, and the like, and others.

Referring now to core member 30, the entire core member 30 can be made of the same material along its length, or in some embodiments, can include portions or sections made of different materials. In some embodiments, the material used to construct core member 30 is chosen to impart varying flexibility and stiffness characteristics to different portions of core member 30. For example, the proximal region and the distal region of core wire 30 may be formed of different materials, for example materials having different moduli of elasticity, resulting in a difference in flexibility. In some embodiments, the material used to construct the proximal region can be relatively stiff for pushability and torqueability, and the material used to construct the distal region can be relatively flexible by comparison for better lateral trackability and steerability. For example, the proximal region can be formed of straightened 304v stainless steel wire or ribbon and the distal region can be formed of a straightened super elastic or linear elastic alloy, for example a nickel-titanium alloy wire or ribbon.

In embodiments where different portions of core member 30 are made of different materials, the different portions can be connected using any suitable connecting techniques. For example, the different portions of core member 30 can be connected using welding (including laser welding), soldering, brazing, adhesive, or the like, or combinations thereof. Additionally, some embodiments can include one or more mechanical connectors or connector assemblies to connect the different portions of core member 30 that are made of different materials. The connector may include any structure generally suitable for connecting portions of a guidewire. One example of a suitable structure includes a structure such as a hypotube or a coiled wire which has an inside diameter sized appropriately to receive and connect to the ends of the proximal portion and the distal portion. Some other examples of suitable techniques and structures that can be used to interconnect different shaft sections are disclosed in U.S. patent application Ser. No. 09/972,276 filed on Oct. 5, 2001, Ser. No. 10/068,992 filed on Feb. 28, 2002, and Ser. No. 10/375,766 filed on Feb. 26, 2003, which are incorporated herein by reference.

Core member 30 can have a solid cross-section, for example a core wire, but in some embodiments, can have a hollow cross-section. In yet other embodiments, core member 30 can include a combination of areas having solid cross-sections and hollow cross sections. Moreover, core member 30, or portions thereof, can be made of rounded wire, flattened ribbon, or other such structures having various cross-sectional geometries. The cross-sectional geometries along the length of core member 30 can also be constant or can vary. For example, FIG. 1 depicts core member 30 as having a round cross-sectional shape. It can be appreciated that other cross-sectional shapes or combinations of shapes may be utilized without departing from the spirit of the invention. For example, the cross-sectional shape of core member 30 may be oval, rectangular, square, polygonal, and the like, or any suitable shape. Additionally, the core member 30 may include one or more tapered portions, for example, to provide for desired flexibility characteristics. Such tapers can be made or exist in a linear, stepwise, curvilinear, or other suitable fashion to achieve the desired results. For example, in the embodiment shown in FIG. 2, the core member 30 includes a plurality of tapered sections and constant diameter sections.

In some embodiments, a sheath and/or coating, for example a lubricious, a hydrophilic, a protective, or other type of material may be applied over portions or all of the core member 30 and/or tubular member 20, or other portions of device 10. Some examples of suitable polymer sheath materials may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNIFEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like.

In some embodiments sheath material can be blended with a liquid crystal polymer (LCP). For example, the mixture can contain up to about 6% LCP. This has been found to enhance torqueability. By employing selection of materials and processing techniques, thermoplastic, solvent soluble, and thermosetting variants of these and other materials can be employed to achieve the desired results. Some examples of suitable coating materials may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Some coating polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference. Some examples of coatings would be disposing a coating on the thread member(s) and/or all or a portion of the tubular member and/or all or a portion of the core member.

A coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

The length of the guidewire 10 is typically dictated by the length and flexibility characteristics desired in the final medical device. For example, proximal section 12 may have a length in the range of about 20 to about 300 centimeters or more, the distal section 14 may have a length in the range of about 3 to about 50 centimeters or more, and the medical device 10 may have a total length in the range of about 25 to about 350 centimeters or more. It can be appreciated that alterations in the length of sections and/or of the guidewire 10 as a whole can be made without departing from the spirit of the invention.

It should also be understood that a broad variety of other structures and/or components may be used in the guidewire construction. Some examples of other structures that may be used in the guidewire 10 include one or more coil members, braids, shaping or safety structures, such as a shaping ribbon or wire, marker members, such as marker bands or coils, centering structures for centering the core wire within the tubular member, such as a centering ring, an extension system, for example, to effectively lengthen the guidewire for aiding in exchanging other devices, or the like, or other structures. Those of skill in the art and others will recognize that the materials, structure, and dimensions of the guidewire may be dictated primary by the desired characteristics and function of the final guidewire, and that any of a broad range of materials, structures, and dimensions can be used.

In a further embodiment, any of the tubular members described herein can also be incorporated into devices other than the guidewires that have been shown. As one example, any of the tubular members mentioned herein can be incorporated into a catheter shaft. In some cases, incorporating such tubular members into a catheter shaft can aid a catheter in crossing a lesion. For example, a catheter shaft with threads on a distal portion, and/or on the distal end, of the shaft can aid the catheter in crossing an occlusion.

In yet another embodiment, a method of making a device is disclosed. A tubular member with thread members disposed thereon, and optionally slots formed therein, can be formed by any of the methods described above. The tubular member with thread members, and optionally slots, can be incorporated into a medical device, for example a catheter or a guidewire. In one example, such a tubular member can define a lumen, and a core member can be at least partially placed within the lumen. The core member and the tubular member can then be attached to one another, for example in a manner disclosed herein. A tip structure can also be placed on the distal end of the device, for example at the distal end of the tubular member and/or the core member.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification. It should be understood that this disclosure is, in many respects, only illustrative. Changes may be made in details, particularly in matters of shape, size, and arrangement of steps without exceeding the scope of the invention. For example, although set forth with specific reference to guidewires in some of the example embodiments shown in the Figures and discussed above, the invention may relate to virtually any medical device including an elongate tubular member having a distal section including a plurality of angled slots defined therein that form a generally spiral shaped pattern about the longitudinal axis. Such structure may aid a user of the device in crossing an occlusion in a blood. For example, the invention may be applied to medical devices such as a balloon catheter, an atherectomy catheter, a drug delivery catheter, a stent delivery catheter, an endoscope, a fluid delivery device, other infusion or aspiration devices, delivery (i.e. implantation) devices, and the like. Thus, while the Figures and descriptions above are directed toward a guidewire, in other applications, sizes in terms of diameter, width, and length may vary widely, depending upon the desired properties of a particular device. The scope of the invention is, of course, defined in the language in which the appended claims are expressed.

What is claimed is:

1. A medical guidewire comprising:
an elongated tubular member including a proximal region having a proximal end and a distal region having a distal end, the tubular member defining an inner lumen and having an outer surface, at least the distal region of the tubular member including a plurality of slots formed and defined by the tubular member that are configured to increase a lateral flexibility of the tubular member;
a core member attached to the tubular member, the core member including a proximal region having a proximal end and a distal region having a distal end, wherein at least a portion of the core member is disposed within the lumen of the tubular member, wherein the distal end of the tubular member extends distally beyond the distal end of the core member; and
one or more thread member disposed on the outer surface of the tubular member and configured such that when the tubular member is rotated about a longitudinal axis, the one or more thread member is capable of engaging an occlusion in a vessel of a patient and pulling at least a portion of the tubular member through the occlusion.

2. The guidewire of claim 1, wherein the one or more thread member is disposed on the distal region of the elongated tubular member.

3. The guidewire of claim 1, wherein the one or more thread member is disposed adjacent the distal end of the elongated tubular member.

4. The guidewire of claim 1, wherein the one or more thread member is disposed in a spiral manner radially about the outer surface of the tubular member.

5. The guidewire of claim 4, wherein the elongated tubular member includes a longitudinal axis, and the one or more thread member is disposed in a spiral manner about the outer surface of the tubular member such that the one or more thread member makes at least one full revolution radially about the longitudinal axis.

6. The guidewire of claim 5, wherein the elongated tubular member includes a longitudinal axis, and the one or more thread member is disposed in a spiral manner about the outer surface of the tubular member such that the one or more thread member makes a plurality of revolutions radially about the longitudinal axis.

7. The guidewire of claim 4, wherein the elongated tubular member includes a longitudinal axis, and the one or more thread members is disposed in a spiral manner about the outer surface of the tubular member such that the one or more thread member makes less than one full revolution radially about the longitudinal axis.

8. The guidewire of claim 1, wherein the elongated tubular member includes a longitudinal axis and plurality of thread sections are disposed in a spiral manner about the outer surface of the tubular member such that each of the plurality of thread sections makes at least one full revolution radially about the longitudinal axis, wherein two or more of the plurality of thread sections together form a thread member.

9. The guidewire of claim 1, wherein the elongated tubular member includes a longitudinal axis and plurality of thread sections are disposed in a spiral manner about the outer surface of the tubular member such that each of the plurality of thread sections makes less than one full revolution radially about the longitudinal axis, wherein two or more of the plurality of thread sections together form a thread member.

10. The guidewire of claim 1, wherein the one or more thread member includes a plurality of thread members.

11. The guidewire of claim 1, wherein the one or more thread member is a separate member attached to the outer surface of the tubular member.

12. The guidewire of claim 1, wherein the one or more thread member is attached to the outer surface of the tubular member by welding, soldering, braising, or adhesive bonding.

13. The guidewire of claim 1, wherein the one or more thread member is of monolithic construction with the tubular member.

14. The guidewire of claim 1, wherein the one or more thread member is formed by a grinding process.

15. The guidewire of claim 1, wherein the one or more thread member comprises a metal, metal alloy, or polymer.

16. The guidewire of claim 1, wherein the proximal region of the tubular member is substantially free of slots formed therein.

17. The guidewire of claim 1, wherein the proximal region of the tubular member includes a plurality of slots formed therein.

18. The guidewire of claim 1, wherein the tubular member comprises a metallic material.

19. The guidewire of claim 1, wherein the tubular member comprises a super-elastic material.

20. The guidewire of claim 1, wherein the tubular member comprises a nickel-titanium alloy.

21. The guidewire of claim 1, wherein the tubular member comprises a linear-elastic nickel-titanium alloy.

22. The guidewire of claim 1, wherein the tubular member comprises a super-elastic nickel-titanium alloy.

23. The guidewire of claim 1, wherein the distal region of the tubular member is more laterally flexible than the proximal region.

24. The guidewire of claim 1, wherein the core member comprises a metallic material.

25. A medical device comprising:
an elongated tubular member including a proximal region having a proximal end and a distal region having a distal end, the tubular member defining an inner lumen and having an outer surface, at least the distal region of the tubular member including a plurality of slots formed and defined by the tubular member that are configured to increase a lateral flexibility of the tubular member, wherein the distal region of the tubular member has a distal outer diameter and wherein the proximal region of the tubular member has a proximal outer diameter that is smaller than the distal outer diameter;
one or more thread member disposed on the distal region of the elongated tubular member, the one or more thread member being disposed in a spiral manner radially about the tubular member and being configured such that when a predetermined rotational force is applied to the tubular member, the thread is capable of engaging an occlusion in a vessel of a patient and pulling at least a portion of the tubular member through the occlusion.

26. The medical device of claim 25, wherein the elongated tubular member includes a longitudinal axis, and the one or more thread member is disposed in a helical manner about the outer surface of the tubular member such that the one or more thread member makes at least one full revolution about the longitudinal axis.

27. The guidewire of claim 25, wherein the elongated tubular member includes a longitudinal axis and plurality of thread sections are disposed in a spiral manner about the outer surface of the tubular member such that each of the plurality of thread sections makes at least one full revolution radially about the longitudinal axis, wherein two or more of the plurality of thread sections together form the one or more thread member.

28. The guidewire of claim 25, wherein the elongated tubular member includes a longitudinal axis and plurality of thread sections are disposed in a spiral manner about the outer surface of the tubular member such that each of the plurality of thread sections makes less than one full revolution radially about the longitudinal axis, wherein two or more of the plurality of thread sections together form the one or more thread member.

29. The guidewire of claim 25, wherein the one or more thread member includes a plurality of thread members.

30. A guidewire for crossing an occlusion in a vessel lumen of a patient, the guidewire comprising:
an elongated tubular member including a proximal region having a proximal end and a distal region having a distal end, the tubular member defining an inner lumen and having an outer surface, at least a portion of the tubular member including a plurality of slots formed and defined by the tubular member that are adapted to increase a lateral flexibility of the tubular member, wherein the distal region of the tubular member has a distal outer diameter and wherein the proximal region of the tubular member has a proximal outer diameter that is smaller than the distal outer diameter;
means for engaging the occlusion and pulling at least a portion of the guide wire through the occlusion when a predetermined twisting motion is applied to the guidewire.

31. The guidewire of claim 30, further including a core member attached to the tubular member, the core member including a proximal region having a proximal end and a distal region having a distal end, wherein at least a portion of the core member is disposed within the lumen of the tubular member.

32. A method of making a guidewire, the method comprising:
providing an elongated tubular member including a proximal region having a proximal end and a distal region having a distal end, the tubular member defining an inner lumen and having an outer surface, at least the distal region of the tubular member including a plurality of slots formed and defined by the tubular member that are configured to increase a lateral flexibility of the tubular member, the tubular member further including one or more thread member disposed on the outer surface of the tubular member and configured such that when the tubular member is rotated about a longitudinal axis, the one or more thread member is capable of engaging an occlusion in a vessel of a patient and pulling at least a portion of the tubular member through the occlusion;
disposing at least a portion of a core member within the lumen of the tubular member;
wherein at least one of the tubular member and the core member, includes a linear elastic nickel titanium alloy;

wherein the core member has a distal end that is disposed proximally of the distal end of the tubular member; and attaching the core member to the tubular member.

33. A method of making a guidewire, the method comprising:

providing an elongated tubular member including a proximal region having a proximal end and a distal region having a distal end, the tubular member defining an inner lumen and having an outer surface, wherein the distal region of the tubular member has a distal outer diameter and wherein the proximal region of the tubular member has a proximal outer diameter that is smaller than the distal outer diameter;

creating a plurality of slots in a portion of the tubular member, the slots being formed and defined by the tubular member, the slots being configured to increase a lateral flexibility of the tubular member; and creating one or more thread member on the outer surface of the tubular member, the thread member being configured such that when the tubular member is rotated about a longitudinal axis, the one or more thread member is capable of engaging an occlusion in a vessel of a patient and pulling at least a portion of the tubular member through the occlusion.

34. The method of claim 33, further including:

providing a core member including a proximal region having a proximal end and a distal region having a distal end;

disposing at least the distal portion of the core member within the lumen of the tubular member; and attaching the core member to the tubular member.

35. The method of claim 33, wherein the one or more thread members are created before the plurality of slots are created.

36. The method of claim 35, wherein the creation of the plurality of slots forms gaps in at least one of the one or more thread members.

37. The method of claim 35, wherein the creation of the plurality slots are formed around the one or more thread members such that none of the plurality of slots cuts through any of the one or more thread members.

38. The method of claim 33, wherein the plurality of slots are created before the one or more thread members are created.

39. The method of claim 38, wherein the creation of the one or more thread members covers at least a portion of at least one of the plurality of slots.

40. The method of claim 38, wherein the creation of the one or more thread members does not cover any of the open areas of any of the plurality of slots.

41. A method for crossing an occlusion in a vessel lumen of a patient, the method comprising:

providing a medical device including an elongated tubular member including a proximal region having a proximal end and a distal region having a distal end, the tubular member defining an inner lumen and having an outer surface, at least the distal region of the tubular member including a plurality of slots formed and defined by the tubular member that are configured to increase a lateral flexibility of the tubular member, the device further including one or more thread member disposed on the distal region of the elongated tubular member adjacent the distal end, the one or more thread member being disposed in a spiral matter radially about the outer surface of the tubular member, wherein the distal region of the tubular member has a distal outer diameter and wherein the proximal region of the tubular member has a proximal outer diameter that is smaller than the distal outer diameter;

inserting the medical device into the vessel;

navigating the medical device to the occlusion such that the distal end of the tubular member engages the occlusion;

applying a rotational force to the medical device such that the one or more thread member on the outer surface of the tubular member engage the occlusion and pull at least a portion of the medical device through the occlusion.

* * * * *

UNITED STATES PATENT AND TRADEMARK OFFICE
CERTIFICATE OF CORRECTION

| | | |
|---|---|---|
| PATENT NO. | : 8,419,658 B2 | Page 1 of 1 |
| APPLICATION NO. | : 11/470452 | |
| DATED | : April 16, 2013 | |
| INVENTOR(S) | : Alan D. Eskuri | |

It is certified that error appears in the above-identified patent and that said Letters Patent is hereby corrected as shown below:

In the Specification

Column 12, Line 11: delete "ARNIFEL®" and insert --ARNITEL®--

Signed and Sealed this
Twenty-ninth Day of October, 2013

Teresa Stanek Rea
*Deputy Director of the United States Patent and Trademark Office*